United States Patent
Bergeron, Jr. et al.

[11] Patent Number: 5,886,051
[45] Date of Patent: Mar. 23, 1999

[54] METHODS AND COMPOSITIONS FOR THE TREATMENT OF NEURODEGENERATION

[75] Inventors: Raymond J. Bergeron, Jr., Gainesville; Stefan Borg, Ponte Vedra Beach, both of Fla.

[73] Assignees: University Of Florida Research Foundation, Inc., Gainesville; SunPharm Corporation, Jacksonville, both of Fla.

[21] Appl. No.: 554,370

[22] Filed: Nov. 8, 1995

[51] Int. Cl.⁶ .......................... A61K 31/13; A61K 31/445
[52] U.S. Cl. .......................... 514/662; 514/660; 514/674; 514/654; 514/316; 514/315
[58] Field of Search ................... 514/674, 649, 514/651, 654, 655, 656, 657, 659, 667

[56] References Cited

U.S. PATENT DOCUMENTS

| | | | |
|---|---|---|---|
| 4,591,605 | 5/1986 | Ray | 514/579 |
| 5,242,947 | 9/1993 | Cherksey et al. | 514/628 |

*Primary Examiner*—Deborah C. Lambkin
*Attorney, Agent, or Firm*—Kerkam, Stowell, Kondracki & Clarke, P.C.; Dennis P. Clarke

[57] ABSTRACT

Methods and pharmaceutical compositions in unit dosage form for treating neurodegeneration in a human or non-human animal afflicted therewith wherein the active agent is a therapeutically effective amount of a polyamine having the formula:

$$R_1-N^1-A-\left[N^2-B\right]_a-\left[N^3-C\right]_b-N^4-R_6 \quad (I)$$
$$\phantom{R_1-N^1-A}\ \ R_2\phantom{-}\ \ \ \ \ R_3\phantom{-]_a}\ \ \ \ R_4\phantom{-]_b}\ R_5$$

or a salt thereof with a pharmaceutically acceptable acid wherein:

$R_1$ and $R_6$ may be the same or different and are hydrogen, alkyl, hydrocarbyl aryl, hydrocarbyl aryl alkyl, cycloalkyl, or any of the foregoing wherein the alkyl chain is interrupted by at least one etheric oxygen atom;

$N^1$, $N^2$, $N^3$ and $N^4$ are nitrogen atoms capable of protonation at physiological pH's;

a and b may be the same or different and are integers from 1 to 4;

A, B and C may be the same or different and are bridging groups of variable length.

23 Claims, 10 Drawing Sheets

Et-4-3-4-Et 1a-d
cis-, or trans-
1,4-, or 1,3-

2a-d
cis-, or trans-
1,4-, or 1,3-

4a-f
cis-, 1,4-, n=4; trans-, 1,4-, n=4
cis-, 1,4-, n=3; trans-, 1,4-, n=3
cis-, 1,3-, n=3; trans-, 1,3-, n=3

5a-f
cis-, 1,4-, n=4; trans-, 1,4-, n=4
cis-, 1,4-, n=3; trans-, 1,4-, n=3
cis-, 1,3-, n=3; trans-, 1,3-, n=3

TRIPROTECTED PUTRESCINE REAGENT

Et-3-4-4-Et

METHODS AND COMPOSITIONS FOR THE TREATMENT OF NEURODEGENERATION

FIELD OF THE INVENTION

The invention relates to compositions and methods for the treatment of neurodegenerative diseases in humans and non-human mammals. In one embodiment, the invention is directed to compositions and methods for alleviating the symptoms associated with neurocognitive disorders, such as senile dementia of the Alzheimer's type.

BACKGROUND

Disorders of cognition are generally characterized by one or more mental symptoms such as forgetfulness, confusion, memory loss, attentional deficits or affective or emotional disturbances. These symptoms may arise as a result of the natural aging process or from organic brain disease, cerebrovascular disease, head injury or developmental or genetic defects. Although cognitive disorders often accompany the general aging process, presenile and senile primary degenerative dementia are the most commonly accepted causes of mental deterioration in the elderly.

Excessive excitation by neurotransmitters can cause the degeneration and death of neurons at any age. The N-methyl-D-aspartate (NMDA) sub-type of the glutamate receptor is a ligand-gated ion channel involved in excitatory neurotransmission in the mammalian central nervous system. For example, over-stimulation of the NMDA receptor results in the neuronal excitotoxicity important in the pathophysiology of epilepsy and ischemia-induced neuron death. Separate regulatory sites on the NMDA receptor-channel complex include the binding site for the agonist L-glutamate, a high-affinity binding site for the obligatory co-agonist glycine, a site where Zn ions act to allosterically inhibit the agonist-induced response independently of membrane potential, a site(s) within the channel wherein Mg ions and phencyclidines such as (+)-5-methyl-10,11-dihydro-5H-dibenzo[a,d]cyclohepten-5,10-imine (MK-801) bind to produce a voltage-dependent open channel block and a distinct binding site for the naturally occurring polyamines, spermine and spermidine.

The polyamine site may exert either agonistic or antagonistic modulatory activity depending on the polyamine concentration, as well as on the chemical structure of the polyamine [Williams et al., Neuron., Vol. 5, pp. 199–208 (1990); Williams et al., Life Sci., Vol. 48, pp. 469–498 (1991)]. Agonists like spermine allosterically facilitate functioning of the L-glutamate and glycine sites resulting in increased binding of [$^3$H]MK-801 compared to that seen in the presence of maximal amounts of L-glutamate and glycine alone. Several compounds that protect neurons from excitotoxicity appear to act as antagonists at the polyamine site [Carter et al., J. Pharmacol. Exp. Ther., Vol. 253, pp. 475–482 (1990); Zeevalk et al., Brain Res., Vol. 522, pp. 135–139 (1990)].

One hypothesis regarding the mechanism of the memory impairment seen in cognitive disorders such as Alzheimer's Disease (AD), the "glutamate hypothesis," suggests that loss of neurotransmission in a glutamatergic system accounts for memory impairment [Greenamyre et al., Neurobiol. Aging, Vol. 10, pp. 593–602 (1989)]. While the exact etiology of AD is not clear, both the level of naturally occurring polyamines and the activity of S-adenosylmethionine decarboxylase, an enzyme important in the biosynthesis of the polyamines, is increased in the brains of AD patients when compared with matched, normal controls [Morrison and Kish, "Brain Polyamine Levels Are Altered in Alzheimer's Disease," Neurosci. Lett., (November 1995); Morrison et al., Neurosci. Lett., Vol. 154, pp. 141–144 (1993)]. Since the natural polyamines can enhance NMDA-mediated excitatory damage by action at the NMDA receptor-channel complex, this increased brain polyamine concentration may be one of the causes of AD.

A major pathological characteristic of AD within the brain is the increased number of amyloid-containing senile plaques having dense cores composed primarily of highly insoluble aggregates of β-amyloid peptide (βA). Transglutaminase enzymes facilitate the formation of insoluble polymers of the β-amyloid peptide [Dudek et al., Brain Res., Vol. 651, pp. 129–133 (1994)]. The naturally occurring polyamines, spermine, spermidine and putrescine, have been shown to be essential to protein cross-linking by transglutaminases in other mammalian systems [Romijn, Andrologia, Vol. 22, Suppl. 1, pp. 83–91 (1990)]. Unusual concentrations of the naturally occurring polyamines in the brains of AD patients may also influence the formation of the senile plaques characteristic of AD and similar dementias.

Only one pharmaceutical composition is currently licensed in the United States as a treatment for Alzheimer's Disease, 9-amino-1,2,3,4-tetrahydroacridine (tacrine). The therapeutic use of tacrine is based upon its activity as an acetylcholinesterase inhibitor, which can increase the availability of acetylcholine as a neurotransmitter. Use of this drug suffers from several drawbacks including limited efficacy and hepatotoxicity [Kaul, J. Pharm. Pharmacol., Vol. 14, pp. 237–242 (1962); Summers et al., New Engl. J. Med., Vol. 315, pp. 1241–1245 (1986)]. Thus, it is of interest to develop novel compositions and methods that are useful for the treatment of Alzheimer's disease and other neurodegenerative conditions.

Relevant Literature

The NMDA receptor has been implicated in the formation of long-term memory potentiation [Muller et al., Science, Vol. 242, pp. 1694–1698 (1988)]. The NMDA receptor is also considered to constitute the electrophysiological manifestation of memory formation [Gustafsson et al., Trends Neurosci., Vol. 22, pp. 156–162 (1988)]. Moreover, antagonism of the NMDA receptor or blockade of the cationic channel of the NMDA receptor impairs acquisition, but not retention performance, of rats in a wide range of tasks [Butelman, Pharmacol. Biochem. Behav., Vol. 34, pp. 13–16 (1989); Lyford et al., Psychobiol., Vol. 19, pp. 157–160 (1991); Morris et al., Nature, Vol. 319, pp. 774–776 (1986); Robinson et al., Psychobiol., Vol. 17, pp. 156–164 (1989); Shapiro et al., Psychobiol., Vol. 18, pp. 231–243 (1990)]. NMDA receptors are highly localized to areas of the brain, the hippocampus and frontal cortex, which have been implicated in learning and memory processing [Monaghan et al., J. Neurosci., Vol. 5, pp. 2909–2919 (1985)].

Munir et al. have stated that the ability of some polyamines to attenuate the excitotoxicity produced by NMDA in a neonatal rat model suggests that these or related compounds may have therapeutic potential as neuroprotective agents [Munir et al., Brain Res., Vol. 616, pp. 163–170 (1993)]. Ingram et al. have suggested that the polyamine site on the NMDA receptor complex can be targeted for pharmacological manipulation to improve learning performance [Ingram et al., Ann. New York Acad. Sci., Vol. 717, pp. 16–32 (1994); Ingram et al., Life Sci., Vol. 55, pp. 2037–2049 (1994)].

It has been suggested that diethylhomospermine interacts with the NMDA receptor in mammalian intestinal tract [Sninsky et al., Gastroenterology, Vol. 106(4)(2), p. A569 (1994)].

Anti-neoplastic derivatives of the naturally occurring polyamines, pharmaceutical compositions and methods of treatment are also disclosed in the following pending patent application Ser. No. 08/231,692 filed Apr. 25, 1994, as well as in U.S. Pat. No. 5,091,576 issued Feb. 25, 1992; U.S. Pat. No. 5,128,353 issued Jul. 7, 1992; and U.S. Pat. No. 5,173,505 issued Dec. 22, 1992. The disclosure of the foregoing application and the disclosures of each of the foregoing patents are incorporated herein by reference.

SUMMARY OF THE INVENTION

The present invention provides methods and compositions for modulating cognitive or motor function in a neurologically compromised mammalian host. The methods include administering an amount of a polyamine or a salt thereof sufficient to alleviate the symptoms of cognitive or motor function deterioration. The polyamine can be provided in a variety of pharmaceutically acceptable formulations and has the formula:

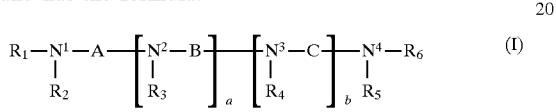

or a salt thereof with a pharmaceutically acceptable acid wherein:

$R_1$–$R_6$ may be the same or different and are hydrogen, alkyl, hydrocarbyl aryl, hydrocarbyl aryl alkyl, cycloalkyl, or any of the foregoing wherein the alkyl chain is interrupted by at least one etheric oxygen atom;

$N^1$, $N^2$, $N^3$ and $N^4$ are nitrogen atoms capable of protonation at physiological pH's;

a and b may be the same or different and are integers from 1 to 4;

A, B and C may be the same or different and are bridging groups of variable length.

In one embodiment of the present invention, abnormal intracellular concentrations of one or more of the naturally occurring polyamines, spermidine, putrescine and spermine, at the polyamine recognition site of the NMDA receptor-channel complex are changed by administration of a therapeutically effective amount of the polyamine of Formula I. The therapeutically effective amount is preferably sufficient to modulate naturally occurring polyamine levels in mammalian brains to levels substantially free from NMDA-mediated cytotoxicity.

In another embodiment of the invention, an amount of polyamine of Formula I sufficient to down-regulate enzymatic production pathways of the naturally occurring polyamines, spermidine, putrescine and spermine, in an affected mammalian host and to decrease any deleterious effect of these polyamines at the NMDA receptor-channel complex is administered.

In a further embodiment, the intracellular concentration of the polyamine of Formula I is administered at a level at which it acts as an antagonist at the NMDA receptor-channel complex in mammalian brains. The invention finds use in the treatment of Alzheimer's Disease, similar senile dementias, and other neurodegenerative conditions.

DETAILED DESCRIPTION OF THE INVENTION

Figure 1:
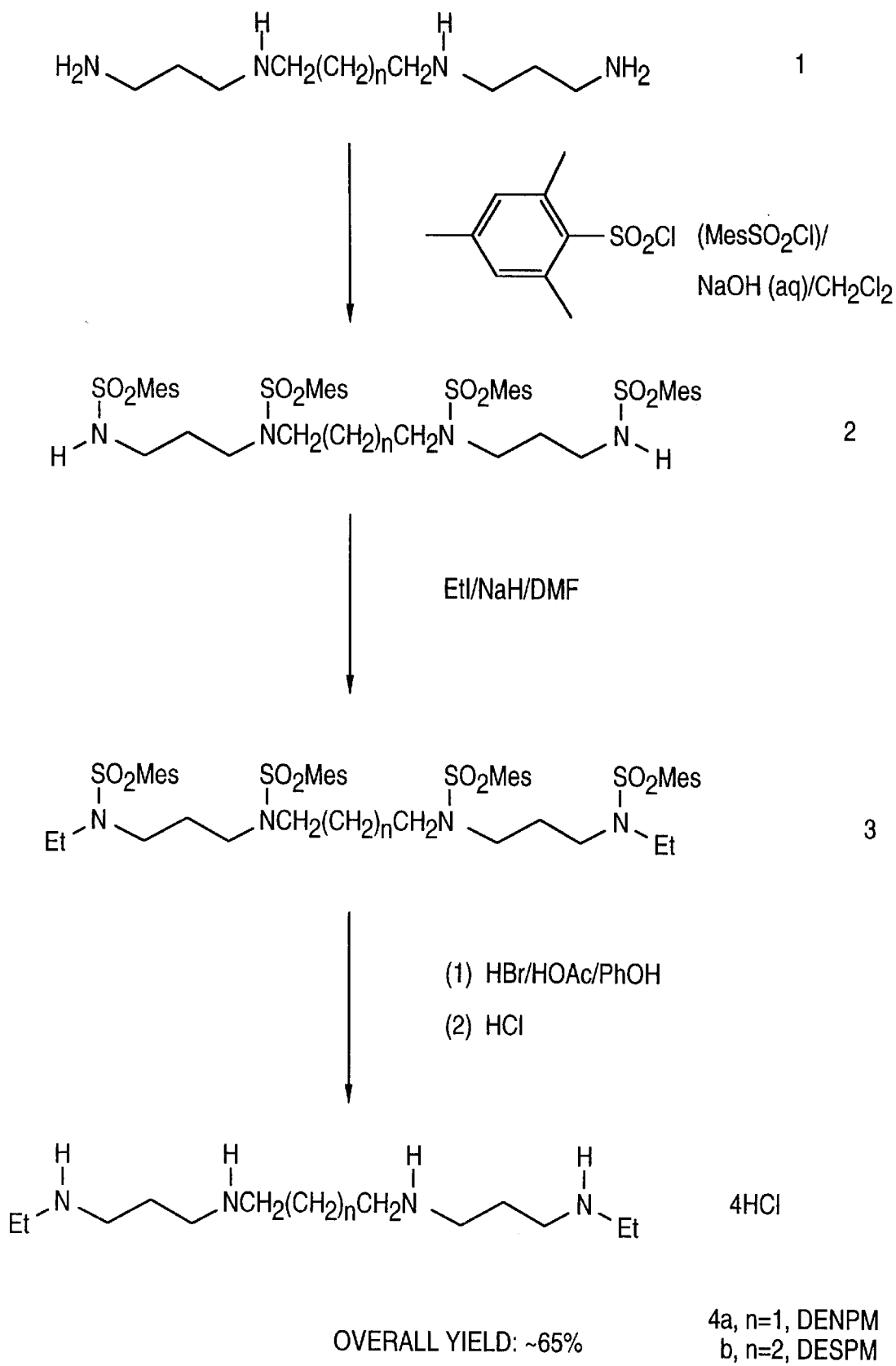
FIGS. 1–8 depict reaction schemes for preparing various polyamines of the invention and intermediates therefor.

The present invention provides a method for modulating neurological function in a compromised mammalian host by administering a therapeutically effective amount of a pharmaceutical composition comprising a polyamine of Formula I. Modulation of neurological function includes both increasing and decreasing of the function, depending upon whether enhancement or diminishment provides a positive outcome. The compromised mammalian host can be any human or non-human mammal showing signs of neurological dysfunction that can be ameliorated by adjustment of naturally occurring polyamines below a level at which they stimulate NMDA-mediated cytotoxicity. The neurological dysfunction can be characterized by difficulties in motor or cognitive function, as measured by techniques known to those skilled in the art.

In one embodiment of the invention, symptoms of cognitive decline in the elderly are treated. Patients suffering from non-specific memory impairment associated with aging can benefit from treatment with the invention, as well as those who can be diagnosed with specific conditions including Alzheimer's Disease, senile dementia, Pick's disease, Huntington's chorea, tardive dyskinesia, hyperkinesia, mania, or similar conditions of cerebral insufficiency. Senile dementia of the Alzheimer's type, also characterized as Alzheimer's presenile and senile onset dementias, has various symptoms including cognitive symptoms such as amnesia, aphasia, apraxia, agnosia, impairment in judgment and abstract thinking, and non-cognitive symptoms, such as behavioral disturbances, anxiety, aggressiveness and depression. Depending upon the response of an individual patient, improvement in one or more of these manifestations of neuro-degeneration is provided by the present invention. The methods of the invention are preferably used in patients in the early stages of impairment so that further neuronal damage can be modulated or prevented.

In the present invention, "polyamine" means all compounds having a structure according to Formula I. "Naturally occurring polyamines" means the aliphatic amines putrescine, spermidine and spermine. These compounds have many known biological effects. Biosynthesis of polyamines in mammalian cells is highly regulated by ornithine decarboxylase (ODC), an enzyme which catalyzes the decarboxylation of ornithine to putrescine, and S-adenosylmethionine decarboxylase (SAMDC), which catalyses the decarboxylation of S-adenosylmethionine (SAM) to form decarboxylated SAM, the donor of aminopropyl groups in the synthesis of spermidine from putrescine, and spermine from spermidine [Gilad et al., Biol. Psychiatry, Vol. 38, pp. 227–234 (1995)]. Administration of the polyamine of Formula I shuts down metabolism of the naturally occurring polyamines, thus reducing cellular concentrations of the naturally occurring polyamines. Thus, in one embodiment, a therapeutically effective amount of the polyamine of the present invention is that which reduces the quantities of intracellular naturally occurring polyamines by interfering with the activity of enzymes involved in their biosynthesis such as ODC and SAMDC.

In another embodiment of the present invention, a therapeutically effective amount of the polyamine of Formula I can be characterized by its activity at the NMDA receptor-channel complex. The naturally occurring polyamines modulate NMDA receptor function with putrescine being an endogenous antagonist and spermine being an agonist that facilitates increased binding of MK-801, a known non-competitive NMDA-receptor antagonist with protective effects against excitotoxic amino acid-induced neuronal degeneration. The polyamines of the present invention exhibit a pronounced biphasic action on NMDA-receptor function displaying agonist activity similar to spermine at lower amine concentrations, but inhibition of [$^3$H]MK-801 binding in a manner similar to that described for inverse agonists at higher concentrations. Thus, a therapeutically effective amount is that sufficient to exert an agonist activity, but more than that required to exert an antagonist activity, at the polyamine recognition site on the NMDA receptors of the neurologically compromised individual. Such a dosage level would provide enough polyamine of Formula I to adjust the concentration of the naturally occurring polyamines in the brain to normal levels so as to prevent their neurotoxic behavior at the NMDA receptor, thus preventing the progress of AD or similar conditions.

In another embodiment, the present invention is a method of therapeutic treatment of disorders resulting from the over-stimulation of the NMDA receptor and consequent neuronal excitotoxicity. Such disorders include cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma. Also included are epilepsy and neurodegenerative disorders such as Huntington's disease and Parkinson's disease.

In the polyamines of the invention, as described in Formula I, $R_1$–$R_6$ may be alkyl, for example, methyl, ethyl, n-propyl, isopropyl, n-butyl, isobutyl, sec-butyl, tert-butyl and the like; hydrocarbyl aryl, for example, phenyl, p-tolyl, 2,4,6-trimethylphenyl and the like; hydrocarbyl aryl alkyl, for example, benzyl, α-phenethyl, β-phenethyl and the like; cycloalkyl, for example, cyclohexyl, cyclobutyl, cyclopentyl, cycloheptyl and the like; any of the foregoing wherein the alkyl chain is interrupted by etheric oxygen, for example, $CH_3O(CH_2)_2$—, $CH_3O(CH_2)_2O(CH_2)_2$—, $CH_3O(CH_2)_2O(CH_2)_2O(CH_2)_2$— and the like; or hydrogen.

At physiological pH's, the naturally occurring polyamines and the analogues of the present invention are largely in a protonated state [Bergeron et al., Bioorg. Chem., Vol. 14, pp. 345–355 (1986)]. Except where $R_1$–$R_6$ are hydrogen or etheric substituents, each R group is hydrocarbyl and may have from about 1 to about 12 carbon atoms, it being understood that the size of the substituents will be tailored in each case to ensure that the polyamine is capable of being protonated at a physiological pH.

The bridging groups of variable length, A, B and C, may be the same or different and may be alkylene having 1–8 carbon atoms, for example, methylene, trimethylene, tetramethylene, pentamethylene and the like; branched alkylene, for example, —CH(CH$_3$)CH$_2$CH$_2$—, —CH$_2$CH(CH$_3$)CH$_2$—, —CH(CH$_3$)CH$_2$CH$_2$—, —CH$_2$CH(CH$_3$)CH$_2$CH$_2$— and the like; hydrocarbyl arylalkylene, for example, —CH(Ph)CH$_2$CH$_2$—, —CH$_2$CH(Ph)CH$_2$—, —CH(Ph)CH$_2$CH$_2$CH$_2$—, —CH$_2$CH(Ph)CH$_2$—CH$_2$— and the like; cycloalkylene, for example, cyclohexylene, cis- and trans-1,3-cyclohexylene, 1,4-cyclohexylene, 1,3-cyclopentylene and the like; heterocyclic groups which incorporate within the ring one of the nitrogen atoms of the polyamine [for example,

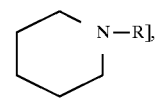

it being understood that the heterocyclic nitrogen group may be located at the terminal end(s) or within the interior of the polyamine.

Particularly preferred polyamines are those set forth in Table 1 and in the examples, as well as those having the formula:

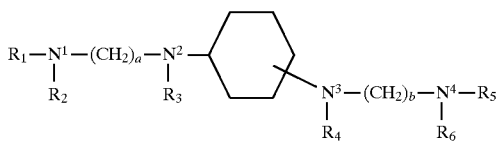

wherein $R_1$–$R_6$ have the meanings ascribed above and a and b may be the same or different and are integers from 2 to 8.

TABLE 1

Analogue

EtNH~~~~N(H)~~[cyclohexyl, trans, N(H)]~~N~~~~NHEt·4HCl

TABLE 1-continued
Analogue
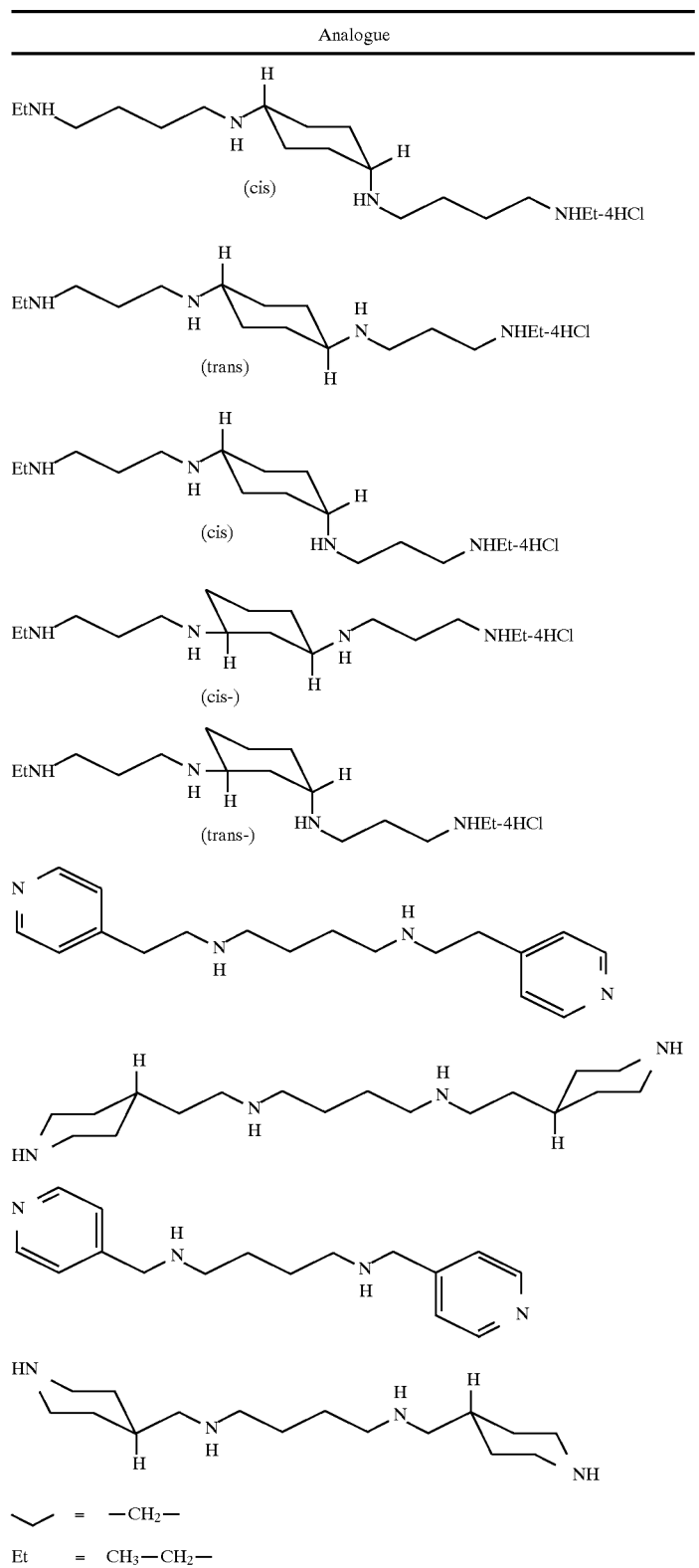
⌄ = —CH₂—
Et = CH₃—CH₂—
Various methods of synthesis of polyamines of Formula I have been previously disclosed [Bergeron et al., J. Org. Chem., Vol. 45, pp. 1589–1592 (1980); Bergeron et al., Synthesis, pp. 732–733 (1981); Bergeron et al., Synthesis, pp. 689–692 (1982); Bergeron et al., Synthesis, pp. 782–785 (1984); Bergeron et al., J. Org. Chem., Vol. 49, p. 2997

(1984); Bergeron, Accts. Chem. Res., Vol. 19, pp. 105–113 (1986); Bergeron, Bioorg. Chem., Vol. 14, pp. 345–355 (1986); Bergeron et al., J. Org. Chem., Vol. 53, pp. 3108–3111 (1988); Bergeron et al., J. Org. Chem., Vol. 52, pp. 1700–1703 (1987); Bergeron et al., J. Org. Chem., Vol. 56, pp. 586–593 (1991); Bergeron et al., CRC Handbook on Microbial Iron Chelates, pp. 271–307 (1991); Bergeron et al., J. Med. Chem., Vol. 37, pp. 3464–3476 (1994); and Bergeron et al., J. Med. Chem., Vol. 38, pp. 425–428 (1995)]. Alternatively, linear polyamines of Formula I, such as DMNSPM, DMHSPM, DENSPM, DEHSPM, DTBHSPM, may be synthesized according to U.S. Pat. Nos. 5,091,576 or 5,342,945, which are incorporated herein by reference. BAHSPM may be synthesized according to the method of Bergeron et al., J. Med. Chem., Vol. 38, pp. 425–428 (1995).

Figure 2:
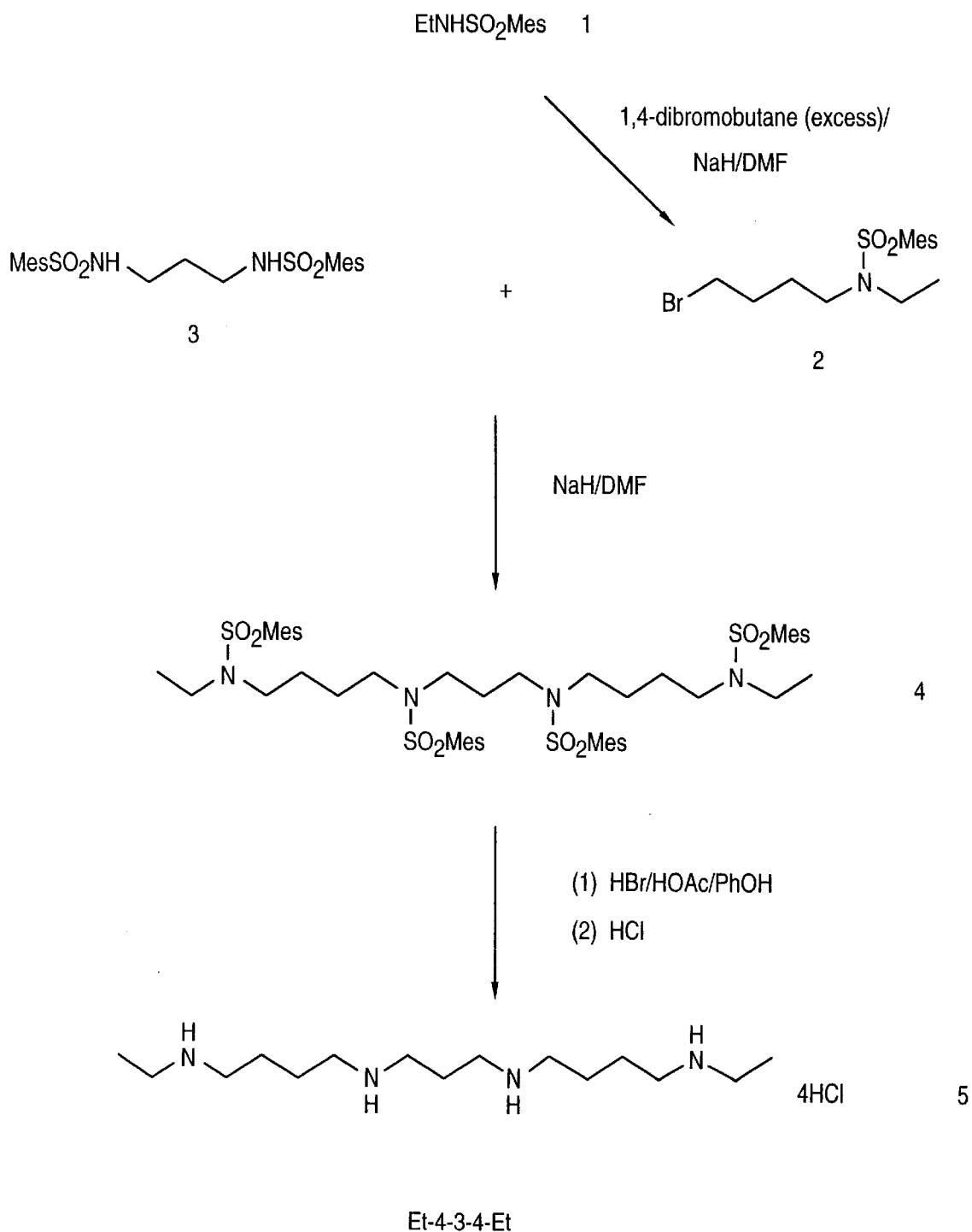

Preferably, linear polyamines of Formula I where bridging groups A, B and C are one or more methylene units, such as DMNSPM, DMHSPM, DENSPM, DEHSPM, DTBHSPM and BAHSPM, or branched alkylene may be synthesized according to the method of U.S. Ser. No. 08/080,642 filed Jun. 22, 1993, now pending, which is incorporated herein by reference. The appropriate tetramesitylenesulfonamide can be alkylated in high yields and the tetramesitylenesulfonyl (MES) protecting groups quantitatively removed by treatment with 30% HBr in acetic acid and phenol as shown in FIG. 1. A "segmented synthesis" approach begins with mesitylenesulfonation of a primary amine providing (1), followed by alkylation of (1) with an excess of the appropriate dihalide (FIG. 2). The resulting halosulfonamide (2) can then be utilized to alkylate the disulfonamides, for example, (3). The tetrasulfonamide (4) is treated with HBr in HOAc/PhOH to remove the mesitylenesulfonamide protecting groups. The resulting bromide is converted to the corresponding HCl salt. Polyamines of Formula I where bridging groups A, B or C are cycloalkylene, such as the trans-1,4-diaminocyclohexane DESPM analogue (5) shown in FIG. 3, or heterocyclic, are also preferably obtained by sulfonation of the appropriate diamine (1) to give a disulfonamide (2), followed by alkylation with two equivalents of halosulfonamide (3, n=3). Finally, the amine protecting groups of tetrasulfonamide (4) are easily removed by treatment with phenol and HBr as above to provide a cyclic spermine analogue.

Figure 4:
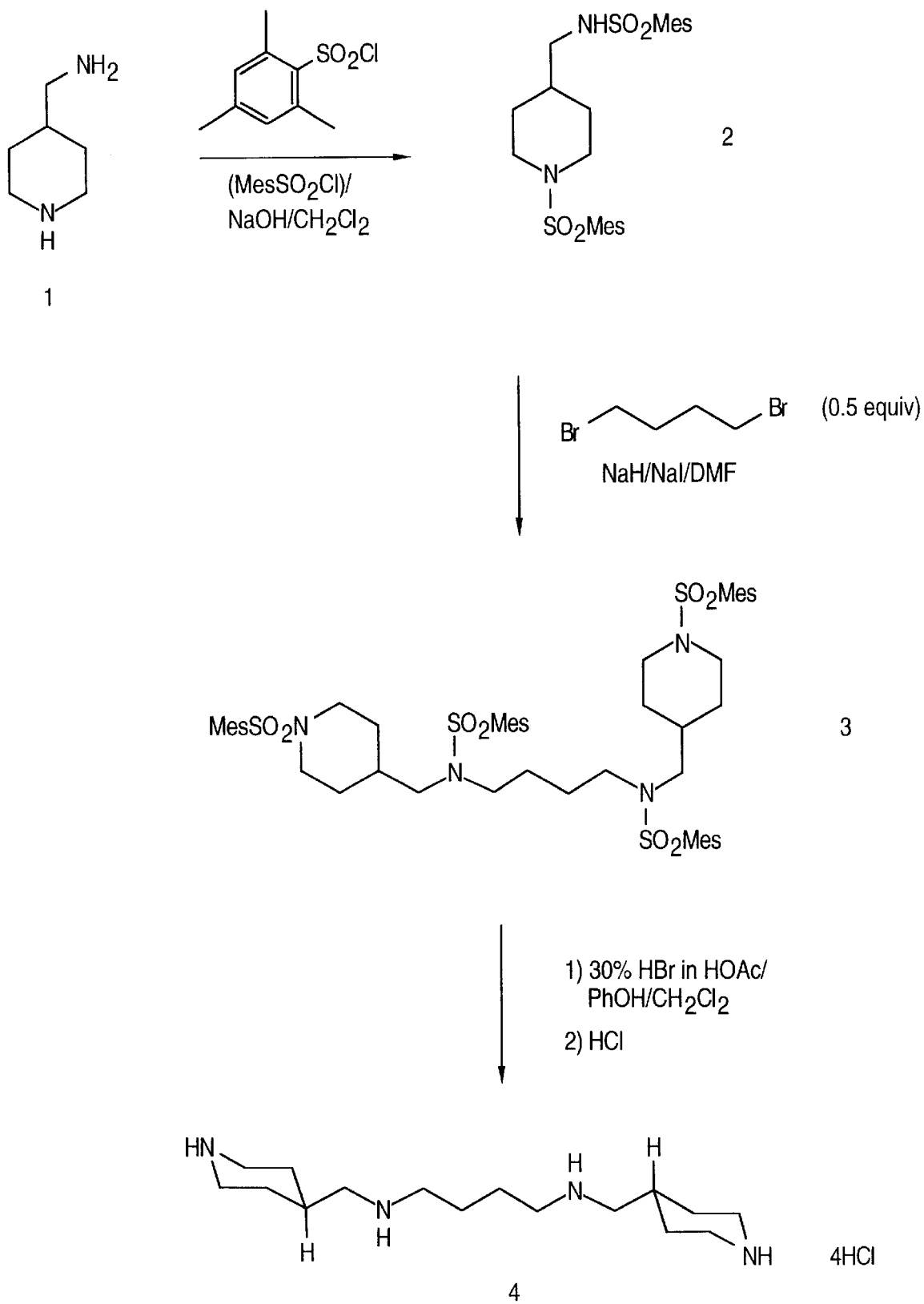
Figure 5:
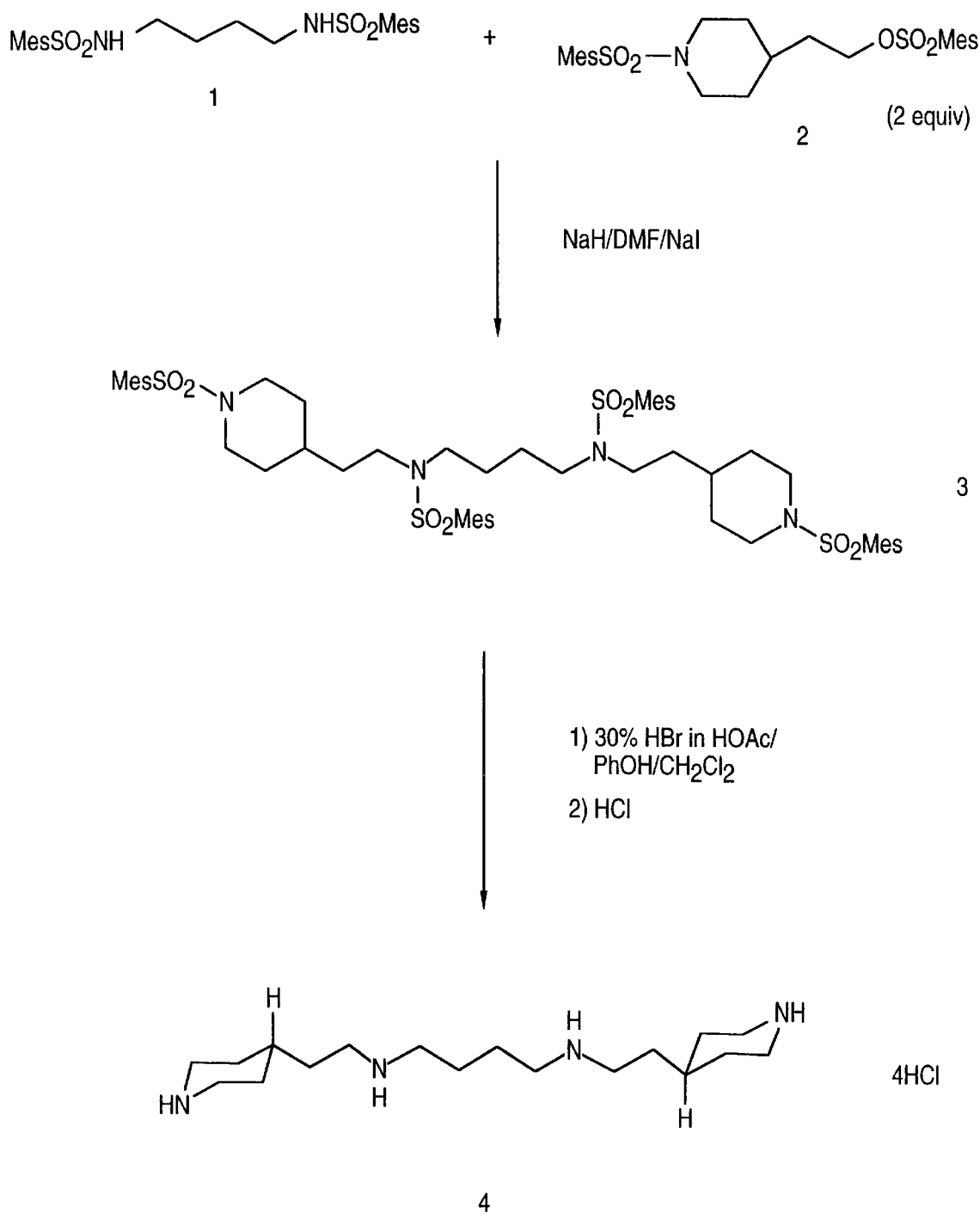

Polyamines of Formula I in which the terminal nitrogens are incorporated into piperidine rings, such as PIP[5,4,5], PIP[4,4,4], PIP[3,4,3] and PIP[3,3,3], may be preferably prepared using mesitylenesulfonyl-protected segments, as shown in FIGS. 4 and 5. For example, a bicyclic DEHSPM analogue (4 in FIG. 4), may be obtained by alkylation with 1,4-dibromobutane (0.5 equivalent)/NaH/DMF of the bis-sulfonamide (2) of 4-(aminomethyl)piperidine (1) to give (3). Reductive removal of the sulfonamide protecting groups with 30% HBr in HOAc/PhOH yields a bicyclic DEHSPM analogue (4) (FIG. 4). As a further example (FIG. 5), the corresponding 5-4-5 bicyclic polyamine may be synthesized by alkylation of N,N'-bis(mesitylenesulfonyl)putrescine (1) with mesitylenesulfonate (2), a solid derived from 4-piperidineethanol and mesitylenesulfonyl chloride (MesSO$_2$Cl) in pyridine. Deprotection of sulfonamide (3) with HBr as usual then gives bicyclic spermine analogue (4).

Use of a tri-protected diamine reagent (FIG. 6) permits synthesis of tetraamines that are unsymmetrical with respect to both their outer methylene chains and terminal alkyl substituents. This methodology eliminates the limitation in earlier routes that the terminal alkyl substituents must be identical. Furthermore, terminal monoethyl polyamines (FIG. 8), which are useful as standards in studies of diethyl analogue metabolism, can also be generated in a systematic way.

Figure 7:
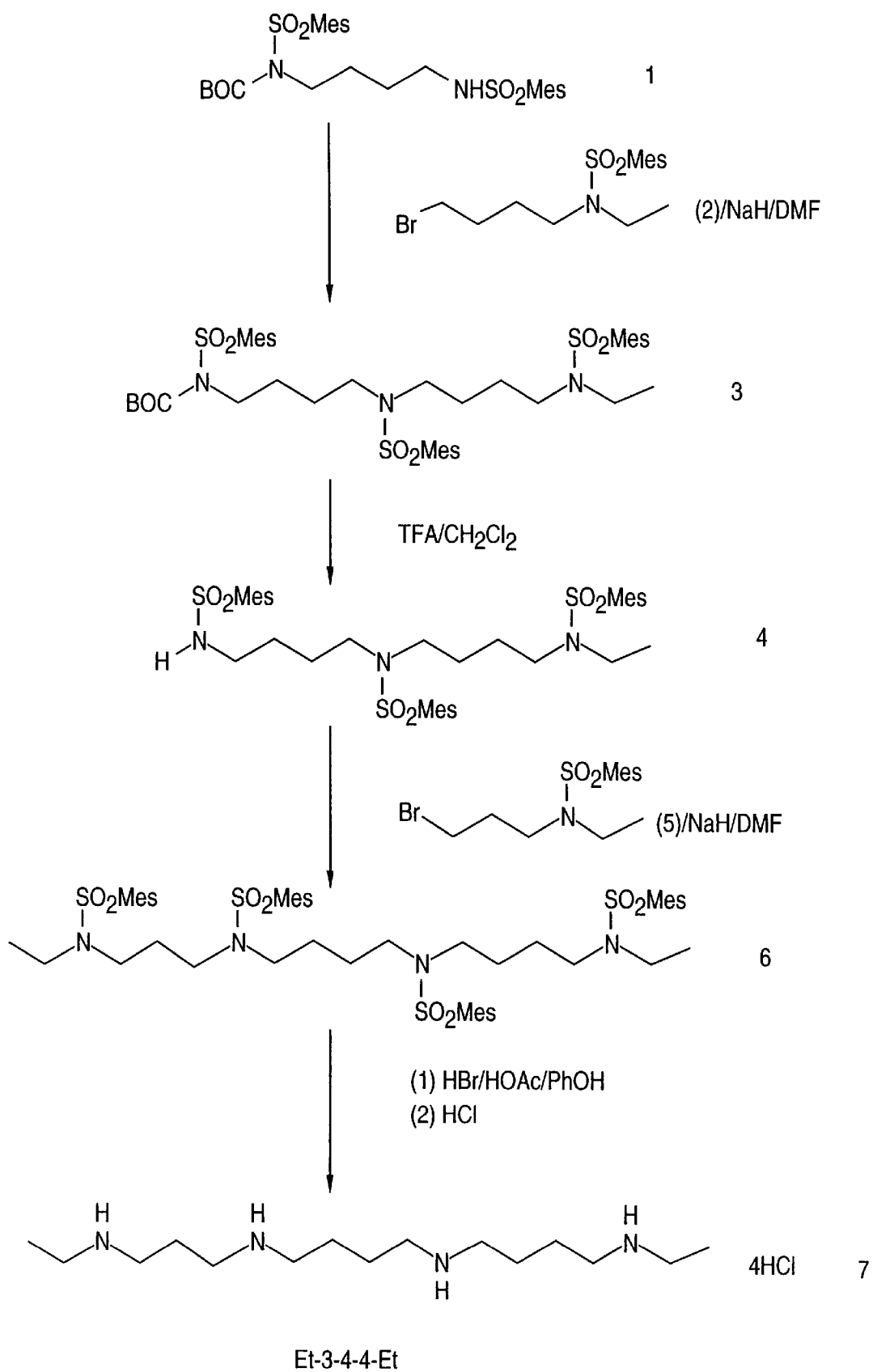
Figure 8:
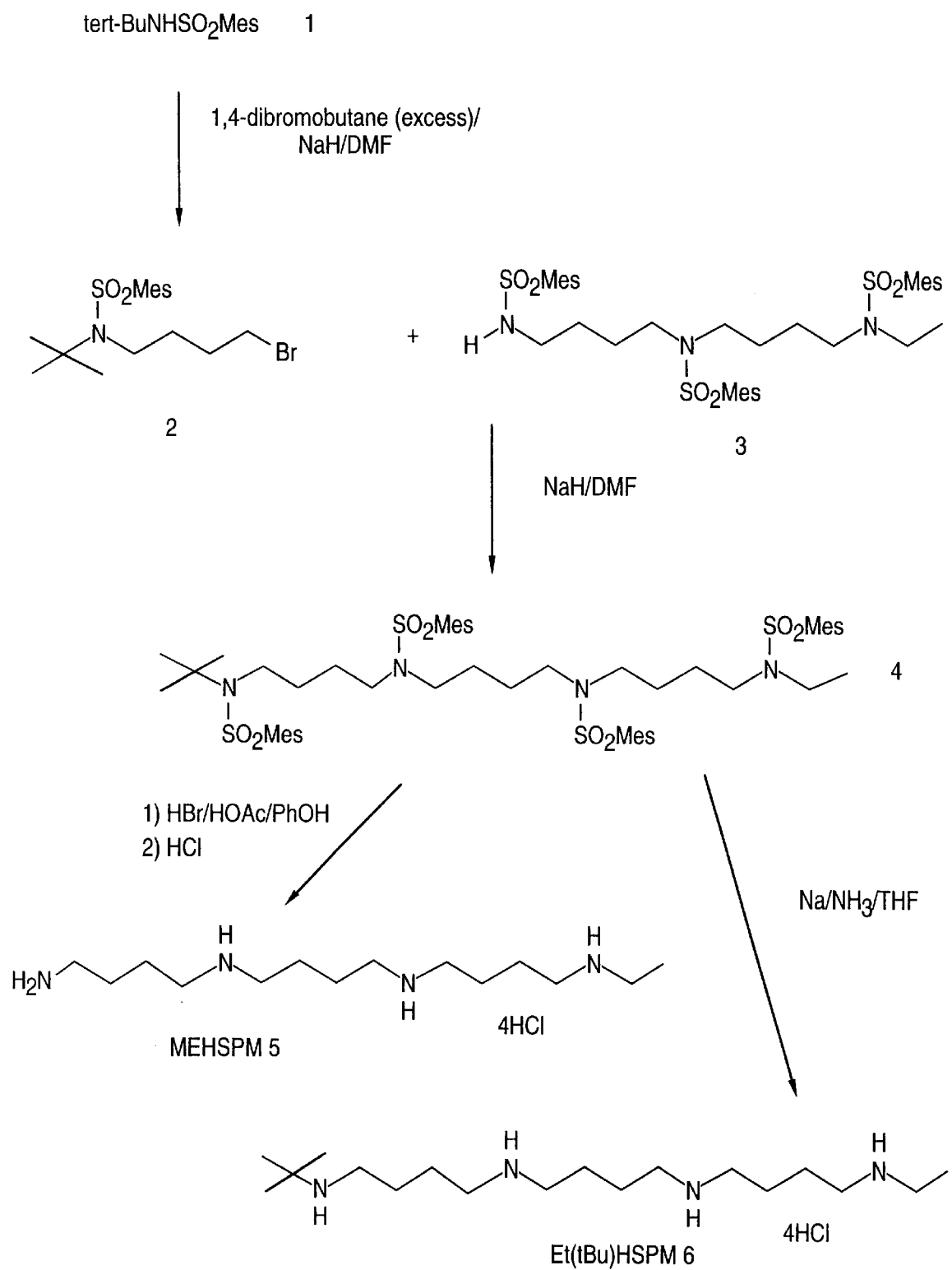
Figure 9:
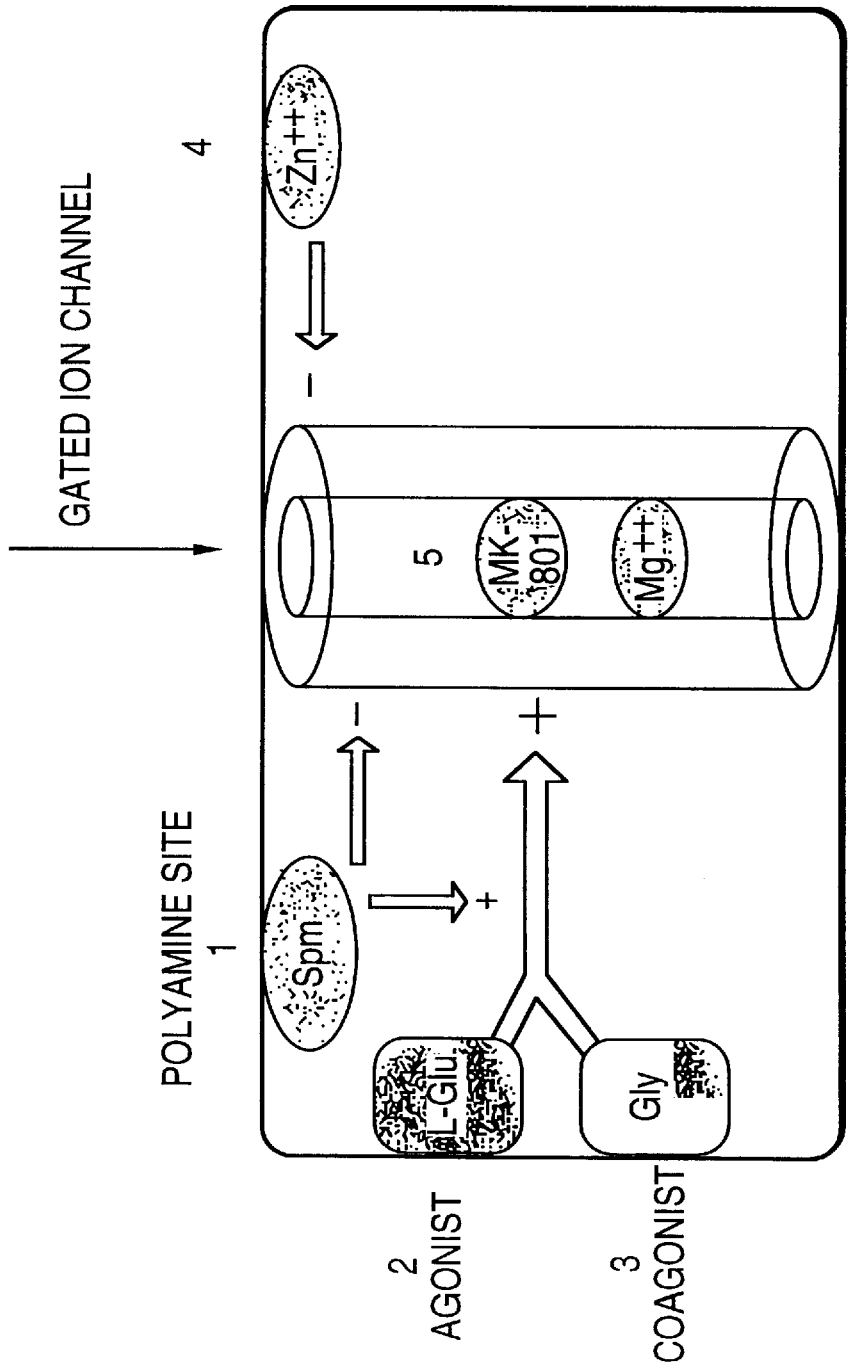
FIG. 9 shows a diagram depicting the mammalian NMDA receptor-complex and some of the ligand binding sites important to receptor function. Numbers indicate binding sites for polyamines (1); L-glutamate (2); glycine (3); $Zn^{2+}$ ion (4); and $Mg^{2+}$ ion (5).
Figure 10:
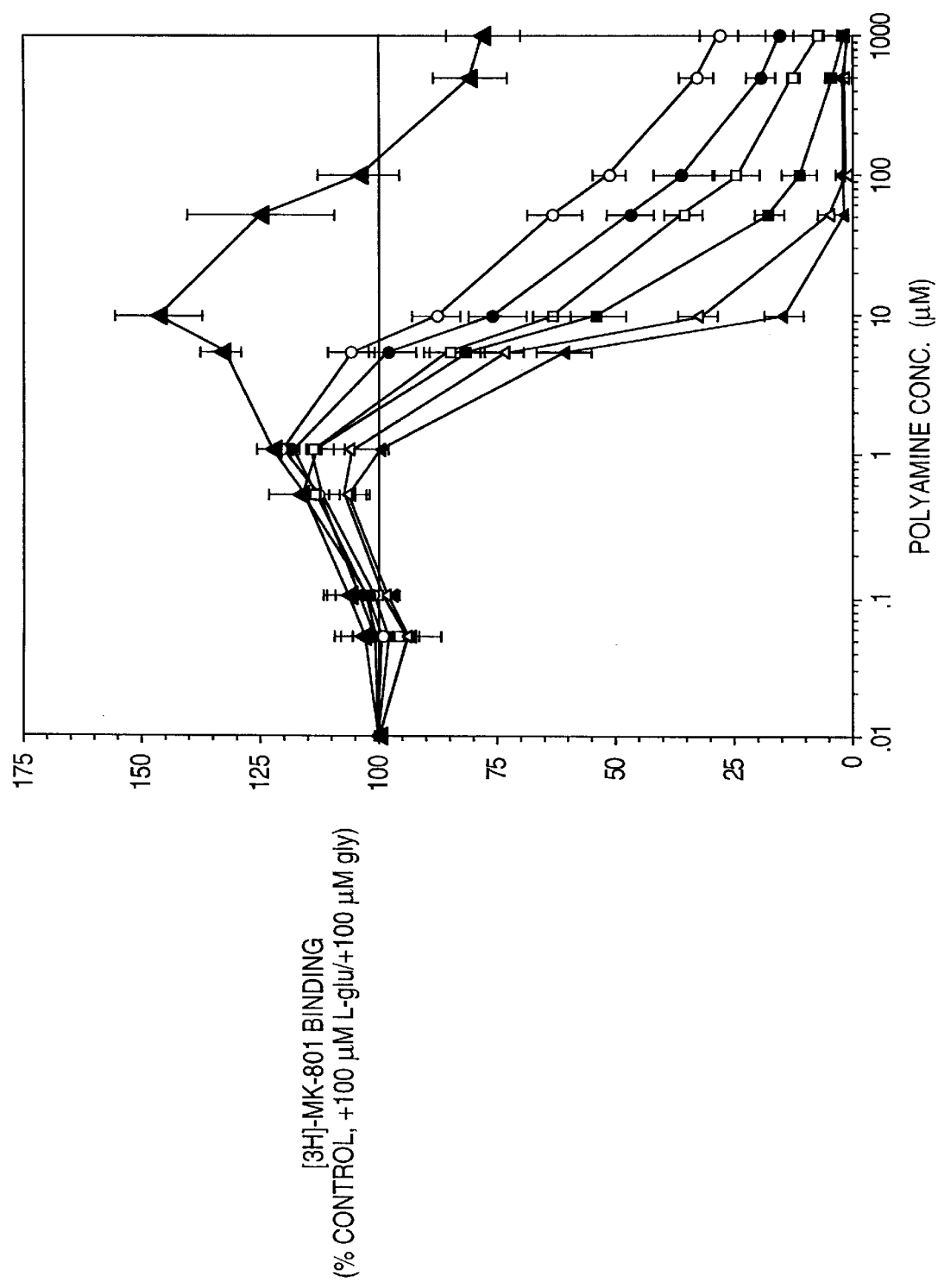
FIG. 10 graphs the results from experiments measuring the binding of [$^3$H]-(+)-5-methyl-10,11-dihydro-5H-dibenzo[a,d]cyclohepten-5,10-imine ([$^3$H]MK-801, 2 nM) to extensively washed rat cortical membranes (ca. 300 μg protein/ml) in the presence of excess L-glutamate (100 μM) and glycine (100 μM) as modulated by spermine and terminally N-alkylated analogues. Data are presented relative to "100% Control" binding observed in the presence of L-glutamate and glycine co-agonists, but absent added polyamine modulator. Data are plotted as means ±standard deviation for four separate experiments on each tetraamine: (—▲—) SPM (n=4), (○) DMNSPM (n=4), (●) DMHSPM (n=4), (□) DENSPM (n=4), (■) DEHSPM (N=4), (Δ) DBHSPM (n=4) and (—▲—) BAHSPM (n=4).

Applications of the tri-protected diamine reagent to unsymmetrical polyamine preparation are shown in FIGS. 7 and 8.

Pharmaceutical compositions comprising the polyamines of Formula I are effective agents in the therapeutic treatment of disorders responsive to agents that modulate the concentrations of naturally occurring neurotoxic polyamines, thus providing a further aspect of the present invention.

For medical use, the amount required of a compound of Formula I or pharmaceutically acceptable salt thereof (hereinafter referred to as the active ingredient) to achieve a therapeutic effect will vary both with the particular compound, the route of administration, the mammal under treatment and the particular disorder or disease concerned. By "active ingredient" is meant a polyamine of Formula I or a salt thereof with a pharmaceutically acceptable acid. By "salt" is meant an addition salt between the polyamine of the invention and a sufficient amount of pharmacologically appropriate acid, such as hydrochloric, sulfuric, phosphoric, acetic, butyric, citric, maleic, lactic, valeric, tartaric, gluconic, succinic and the like, made by conventional chemical means. A suitable systemic dose of the active ingredient for a mammal suffering from any condition as described hereinbefore is in the range of 0.001 to 100 mg of active agent per kilogram of mammal body weight.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by intravenous infusion and repeated administrations, parenterally or orally, as considered appropriate.

While it is possible for an active ingredient to be administered alone, it is preferable to present it as a formulation. Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispensing agent. Molded tablets may be made by molding, in a suitable machine, a mixture of the powdered active ingredient and a suitable carrier moistened with an inert liquid diluent.

Formulations suitable for parenteral administration conveniently comprise a sterile aqueous preparation of the active ingredient which is preferably isotonic with the blood of the recipient.

Formulations suitable for nasal or buccal administration (such as self-propelling powder dispensing formulations described hereinafter) may comprise 0.1 to 20% w/w, for example, 2% w/w of active ingredient.

The formulations, for human medical use, of the present invention comprise an active ingredient in association with a pharmaceutically acceptable carrier therefor and optionally other therapeutic ingredient(s) such as, e.g., cholinergic agents (tacrine, etc.). The carrier(s) must be "acceptable" in the sense of being compatible with the other ingredients of the formulations and not deleterious to the recipient thereof.

The pharmacologically active compounds of the invention are useful in the manufacture of pharmaceutical compositions comprising an effective amount thereof in conjunction or admixture with the excipients or carriers suitable for either enteral or parenteral application. Preferred are tablets and gelatin capsules comprising the active ingredient together with one or more of the following: (a) diluents, such as lactose, dextrose, sucrose, mannitol, sorbitol, cellulose, glycine and the like; (b) lubricants, such as silica, talcum, stearic acid, its magnesium or calcium salt, polyethyleneglycol and the like; for tablets also; (c) binders, such as magnesium aluminum silicate, starch paste, gelatin, tragacanth, methylcellulose, sodium carboxymethylcellulose or polyvinylpyrrolidone and the like; and, if desired, (d) disintegrants, such as effervescent mixtures and the like; and (e) absorbents, colorants, flavors, sweeteners and the like. Injectable compositions are preferably aqueous isotonic solutions or suspensions, and suppositories are advantageously prepared from fatty emulsions or suspensions. Said pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The effectiveness of the polyamine of Formula I for its intended use may be determined in a variety of ways. For example, where the desired effect is the treatment of cognitive disorders such as Alzheimer's Disease, compounds of the invention may be selected for human clinical trials on the basis of data from in vitro and/or in vivo animal models. For example, compound effectiveness can be evaluated in an in vitro bioassay by measuring its action on NMDA-receptor function in the presence of excess obligatory agonists and [$^3$H]MK-801 [Bergeron et al., J. Med. Chem., Vol. 38, pp. 425–428 (1995)]. Compounds exhibiting antagonist activity at the NMDA receptor in this assay are preferred. These same compounds may exhibit agonist activity in this assay at higher concentrations than at those which they exhibit antagonist activity. For such compounds, the therapeutically effective amount administered can be adjusted to provide a positive effect with minimization of any negative effects.

Compound effectiveness can also optionally be tested in animal models. For example, a rat model of age-related memory impairment, the Stone maze model, can be used to test the efficacy of the polyamine of Formula I in cognitive enhancement. This model has been used to test the ability of the physostigmine derivative, phenserine, to improve learning performance of aged rats vs. young rats [Ingram et al., Life Sci., Vol. 55, pp. 2037–2047 (1994)]. Alternatively, transgenic mice expressing high levels of various fragments of human β-amyloid protein, such as those described by Games et al. [Nature, Vol. 373, pp. 523–527 (1995)], can optionally be used to test the efficacy of the polyamine of Formula I.

The general toxicology profile in commonly accepted animal models and bioavailability by the desired route of administration are also considered in the selection of compounds of Formula I.

The efficacy of the methods and compositions of the present invention in the treatment of cognitive disorders such as Alzheimer's Disease can also be evaluated in human clinical trials. Although a definitive AD diagnosis requires post-mortem histopathologic confirmation, generally accepted criteria, known as the DSM-IV, have been designed for screening, defining and categorizing demented patients. The universally recognized and accepted NINCDS-ADRDA criteria [McKhann et al., Neurology, Vol. 34, pp. 939–944 (1984)] may be used in clinical trials to diagnose AD and to evaluate the efficacy of compounds of Formula I. Additionally, the state of the disease before and after treatment may be assessed by various commonly accepted mental-state examinations, including the information-concentration-orientation test of Blessed [Br. J. Psychiatr. Res., Vol. 12, pp. 189–198 (1968)], the Mini Mental State Examination (MMSE) of Folstein et al. [J. Psychiatr. Res., Vol. 12, pp. 189–198 (1975)] and the Global Deterioration Scale of Reisberg [Am. J. Psychiatry, Vol. 140, pp. 734–739 (1983)].

The following examples are offered by way of illustration and not by way of limitation.

EXAMPLES

Polyamine analogues used in the following examples were obtained as follows. DMNSPM, DMHSPM, DENSPM, DEHSPM, DTBHSPM were synthesized according to the method of Bergeron et al., J. Med. Chem., Vol. 37, pp. 3464–3476 (1994). BAHSPM was synthesized according to the method of Bergeron et al., J. Med. Chem., Vol. 38, pp. 425–428. PIP[5,4,5], PIP[4,4,4], PIP[3,4,3] and PIP[3,3,3] were synthesized as described in U.S. Ser. No. 08/080, 642 filed Jun. 22, 1993, now pending. Spermine tetrahydrochloride (SPM) and chemical reagents were purchased from Aldrich Chemical Company. [$^3$H]MK-801 was obtained from Research Biochemical International.

Example 1

Figure 3:
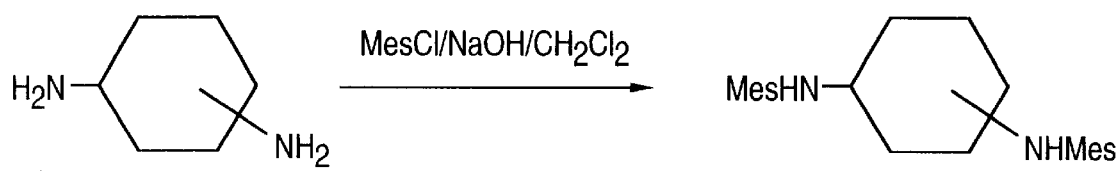
Figure 3:
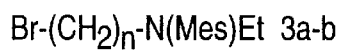
Figure 3:
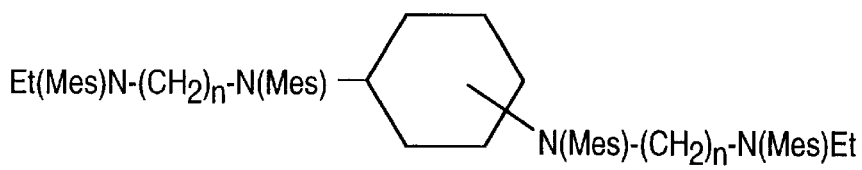
Figure 3:
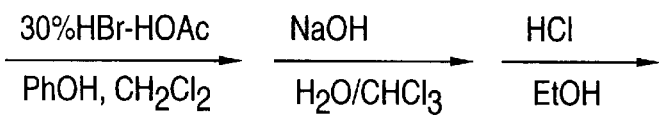
Figure 3:
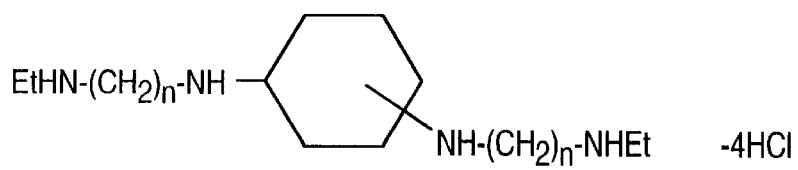

Bis-N,N'-(2-mesitylenesulfonyl)-trans-1,4-cyclohexanediamine [(2a) FIG. 3]

A solution of 2-mesitylenesulfonyl chloride (12.15 g, 55.0 mmol) in 100 ml $CH_2Cl_2$ was slowly dripped into a solution of trans-1,4-diaminocyclohexane (2.92 g, 25.0 mmol) in 100 ml 1N NaOH solution which had been cooled to 0° C. The mixture was stirred at 0° C. for 30 min. and at room temperature overnight. The solid was filtered out and washed with water and ethanol to give 10 g (2a) (82%): mp>300° C.; NMR (DMSO-$d_6$) δ 0.97–1.23 (m, 4H), 1.40–1.63 (m, 4H), 2.20 (s, 6H), 2.50 (s, 12H), 2.63–2.83 (m, 2H).

N-Ethyl-N-(4-bromobutyl)mesitylenesulfonamide [(3b) FIG. 3]

NaH (0.792 g, 80%, 26.4 mmol) was added into a solution of N-ethyl-(2-mesitylenesulfonylamide) (5 g, 22.0 mmol) in 60 ml DMF which had been cooled to 0° C. The mixture was stirred at 0° C. for 30 min. and 1,4-dibromobutane (31.5 ml, 261.4 mmol) was added. The solution was warmed to room temperature for 30 min. and then heated to 80° C. overnight. The DMF was removed and the residue was treated with 40 ml water, followed by extraction with $CH_2Cl_2$ (50 ml×4). The extractions were dried over anhydrous sodium sulfate and the solvent was rotovapped. The crude oil was purified by silica gel column chromatography with 10/1 hexanes/ EtOAc as an eluant to provide 5.85 g (3b) (73%) as an oil; NMR ($CDCl_3$) δ 1.07 (t, J=12, H), 1.60–1.83 (m, 4H), 27 (s, 3H), 2.57 (s, 6H), 3.07–3.37 (m, 6H), 6.90 (s, 2H). Anal. calcd. for $C_{15}H_{24}BrNO_2$: C-49.73, H-6.68, N-3.87. Found: C-49.78, H-6.72, N-3.88.

N,N'-Bis{4-[N''-ethyl,N''(2-mesitylenesulfonyl)] aminobutyl}-trans-1,4-N,N'-bis[(2-mesitylenesulfonyl)amino]cyclohexane [(4a) FIG. 3]

NaH (206.6 mg, 80%, 6.89 mmol) was added into a solution of (2a) (1.5 g, 3.13 mmol) in 40 ml DMF which had been cooled to 0° C. The solution was stirred at 0° C. for 30 min. and the solution of (3b) (2.5 g, 6.89 mmol) in 20 ml DMF was slowly added at 0° C. Then the mixture was stirred at 0° C. for 20 min., at room temperature for 30 min. and at 70° C. overnight, respectively, following the procedure of (3b) above, the residue of which was purified by column chromatography with 5% ethanol in chloroform as an eluant to give 0.93 g (4a) (29%) as an oil; NMR ($CDCl_3$) δ 1.00 (t, J=12, 6H), 1.13–1.43 (m, 4H), 1.73–1.93 (m, 4H), 2.27 (s, 12H), 2.57 (s, 24H), 2.83–3.23 (m, 12H), 3.35–3.67 (m, 2H), 6.90 (s, 8H). Anal. calcd. for $C_{52}H_{76}N_4O_8S_4$: C-61.63, H-7.56, N-5.53. Found: C-61.72, H-7.59, N-5.56.

N,N'-Bis [4-(N''-ethylamino)butyl]trans-1,4-cyclohexanediamine tetrahydrochloride [(5a) FIG. 3]

Phenol (2 g, 21.3 mmol) and 20 ml 30% HBr-HOAc were added into a solution of (4a) (720 mg, 0.69 mmol) in 25 ml $CH_2Cl_2$ and the solution was stirred at room temperature for 24 hours. The solution was diluted with 60 ml $H_2O$ and the $CH_2Cl_2$ layer was separated from the aqueous layer and the aqueous layer was washed by $CH_2Cl_2$ (40 ml×5). The water was removed and the residue was dissolved in 10 ml $H_2O$, basified to pH>12 by the NaOH solution, extracted by $CHCl_3$ (40 ml×5) and dried over sodium sulfate. The salt was filtered out and the solvent was rotovapped. The oil was dissolved in 50 ml EtOH and 1 ml concentrated HCl acid was added. The EtOH was removed and 320 mg crude solid was recrystallized from the mixture of $H_2O$ and EtOH to produce 127 mg (5a) (40%) as nice crystal. NMR ($D_2O$) δ 1.30 (t, J=12, 6H), 1.50–1.67 (m, 4H), 1.67–1.97 (m, 8H), 2.07–2.40 (m, 4H), 2.90–3.40 (m, 14H). Anal. calcd. for $C_{18}H_{44}Cl_4N_4$: C-47.17, H-9.68, N-12.22. Found: C-47.01, H-9.67, N-12.13.

Example 2

N,N'-Bis(2,4,6-trimethylbenzenesulfonyl)-4-(aminomethyl)piperidine [(2) FIG. 4]

A solution of 2-mesitylenesulfonyl chloride (19.49 g, 89.1 mmol) in $CH_2Cl_2$ (100 ml) was added to 4-(aminomethyl) piperidine (1) (5.15 g, 45.1 mmol) in 1N NaOH (100 ml) at 0° C. After the addition was complete, the biphasic mixture was stirred for 24 hours (0° C. to room temperature). The layers were separated and the aqueous portion was extracted with $CHCl_3$ (2×). The combined organic phase was washed with 0.5N HCl (200 ml) and $H_2O$ (100 ml), dried with sodium sulfate and evaporated in vacuo. Recrystallization from aqueous ethanol produced 18.72 g (88%) of (2) as plates: mp 158.5°–160° C.; NMR ($CDCl_3$/TMS) δ 0.8–2.0 (m, 5H), 2.25 (s, 6H), 2.46–2.93 (m+2s, 16H), 3.37–3.65 (m, 2H), 4.67 (t, 1H, J=6), 6.90 (s, 4H). Anal. calcd. for $C_{24}H_{34}N_2O_4S_2$: C-60.22, H-7.16, N-5.85. Found: C-60.31, H-7.19, N-5.86.

N,N'-1,4-Bis(2,4,6-trimethylbenzenesulfonyl) butanediylbis[4-(2,4,6-trimethylbenzenesulfonyl) piperidinemethanamine][(3) FIG. 4]

Sodium hydride (80% in oil, 1.411 g, 47.0 mmol) was added to (2) (18.43 g, 38.5 mmol) and NaI (0.146 g, 0.97 mmol) in DMF (165 ml) at 0° C. The suspension was stirred for 1¾ hours at room temperature under nitrogen. 1,4-Dibromobutane (2.2 ml, 18.4 mmol) was added by syringe and the reaction mixture was heated at 84° C. for 19 hours. After cooling to 0° C., $H_2O$ (200 ml) was cautiously added to quench residual NaH, followed by extraction with $CHCl_3$ (300 ml, 2×100 ml). The combined organic phase was washed with 1% $Na_2SO_3$ (100 ml) and $H_2O$ (2×100 ml), dried with sodium sulfate and evaporated under high vacuum. Recrystallization from EtOAc/$CHCl_3$ gave 13.00 g (70%) of (3) as an amorphous solid: mp 202°–203.5° C.; NMR ($CDCl_3$/TMS) δ 0.75–1.90 (m, 14H), 2.25 (s, 12H), 2.40–3.18 (m+2s, 36H), 3.3–3.6 (m, 4H), 6.87 (s, 8H). Anal. calcd. for $C_{52}H_{74}N_4O_8S_4$: C-61.75, H-7.37, N-5.54. Found: C-61.49, H-7.39, N-5.43.

N,N'-1,4-Butanediylbis(4-piperidinemethanamine) [(4) FIG. 4]

30% HBr in acetic acid (100 ml) was added over 10 min. to a solution of (3) (5.34 g, 5.28 mmol) and phenol (18.97 g, 0.202 mol) in $CH_2Cl_2$ (75 ml) at 0° C. The reaction was stirred for 24 hours (0° C. to room temperature) and cooled to 0° C. Distilled $H_2O$ (120 ml) was added, followed by extraction with $CH_2Cl_2$ (3×100 ml). The aqueous layer was evaporated under high vacuum. The residue was basified with 1N NaOH (12 ml) and 50% (w/w) NaOH (20 ml) with ice cooling, followed by extraction with $CHCl_3$ (10×50 ml), while adding NaCl to salt out the aqueous layer. Organic extracts were dried with sodium sulfate and evaporated. The residue was taken up in ethanol (200 ml), acidified with concentrated HCl (3.5 ml) and solvents were removed under vacuum. Tetrahydrochloride salt was recrystallized with 7% aqueous EtOH to furnish 1.318 g (58%) of (4) as a white solid. NMR ($D_2O$/TSP) δ 1.19–2.23 (m, 14H), 2.8–3.6 (m, 16H). Anal. calcd. for $C_{16}H_{38}Cl_4N_4$: C-44.87, H-8.94, N-13.08. Found: C-44.77, H-9.00, N-13.00.

Example 3

N,N'-Bis(2,4,6-trimethylbenzenesulfonyl)-1,4-butanediamine [(15) FIG. 5]

2-Mesitylenesulfonyl chloride (54.40 g, 0.249 mol) in $CH_2Cl_2$ (300 ml) was added to 1,4-diaminobutane (11.34 g, 0.129 mol) in 1N NaOH (300 ml) at 0° C. and the biphasic mixture was stirred for 24 hours at room temperature. Organic solvent was evaporated and 2.4N HCl (250 ml) was added to the combined portions. Solid was filtered, washed with water (250 ml) and recrystallized from aqueous ethanol to give 50.46 g (90%) of (1) as needles: mp 156.5°–157.50° C.; NMR ($CDCl_3$/TMS) δ 1.36–1.60 (m, 4H), 2.27 (s, 6H), 2.57 (s, 12H), 2.69–2.96 (m, 4H), 4.65 (t, 2H, J=6), 6.89 (s, 4H). Anal. calcd. for $C_{22}H_{32}N_2O_4S_2$: C-58.38, H-7.13, N-6.19. Found: C-58.31, H-7.19, N-6.14.

N,O-Bis(2,4,6-trimethylbenzenesulfonyl)-4-piperidineethanol [(2) FIG. 5]

2-Mesitylenesulfonyl chloride (24.78 g, 0.113 mol) in pyridine (60 ml) was added all at once to 4-piperidineethanol (5.58 g, 43.2 mmol) in pyridine (25 ml) at −16° C.; the temperature rose to −11° C. The flask was stored in the refrigerator at 5.5° C. for 44 hours under argon. The reaction mixture was poured into ice (1 kg) and after 3 hours, 16.00 g (75%) of (2) as a yellow solid was filtered off: mp 93.5°–94° C.; NMR (CDCl$_3$/TMS) δ 1.4–2.1 (m, 7H), 2.27 (s, 6H), 2.44–2.96 (m+s, 14H), 3.37–3.69 (m, 2H), 3.97 (t, 2H, J=5), 6.90 and 6.93 (2s, 4H). Anal. calcd. for $C_{25}H_{35}NO_5S_5$: C-60.82, H-7.15, N-2.84. Found: C-60.90, H-7.13, N2.85.

N,N'-1,4-Bis(2,4,6-trimethylbenzenesulfonyl) butanediylbis[4-(2,4,6-trimethylbenzenesulfonyl) piperidineethanamine][(3) FIG. 5]

Sodium hydride (80% in oil, 0.783 g, 26.1 mmol) was added to (1) (5.15 g, 11.4 mmol) and NaI (0.376 g, 2.5 mmol) in DMF (140 ml) at 0° C. The suspension was stirred for 23 min. at room temperature, followed by the introduction of (2) (15.84 g, 32.1 mmol). The reaction mixture was heated at 58°–67° C. for 18 hours and then poured into H$_2$O (300 ml), followed by extraction with CHCl$_3$ (4×100 ml). The combined extracts were washed with saturated NaHCO$_3$ (100 ml), 1% NaHSO$_3$ (100 ml) and H$_2$O (100 ml), dried with sodium sulfate and evaporated under high vacuum. Column chromatography on silica gel eluting with 1 to 2% CH$_3$OH/CHCl$_3$ furnished 10.03 g (85%) of (3) as an amorphous solid: NMR (CDCl$_3$/TMS) δ 0.8–2.0 (m, 18H), 2.08–2.71 (m+3s, 4OH), 2.8–3.5 (m, 12H), 6.87 (s, 8H). Anal. calcd. for $C_{54}H_{78}N_4O_8S_4 \cdot H_2O$: C-61.33, H-7.62, N-5.30. Found: C-61.50, H-7.44, N-5.33.

N,N'-1,4-Butanediylbis(4-piperidineethanamine) [(4) FIG. 5]

30% HBr in acetic acid (180 ml) was added over 30 min. to a solution of (3) (9.83 g, 9.45 mmol) and phenol (33.38 g, 0.355 mmol) in CH$_2$Cl$_2$ (135 ml) at 0° C. The reaction was stirred for 24 hours (0° C. to room temperature) and cooled to 0° C. Distilled H$_2$O (200 ml) was added, followed by extraction with CH$_2$Cl$_2$ (2×100 ml). The aqueous portion was evaporated under high vacuum. The residue was basified with 1N NaOH (50 ml) and then 50% (w/w) NaOH (10 ml) (ice cooling), followed by extraction with CHCl$_3$ (10×), while adding NaCl to salt out the aqueous layer. Organic extracts were dried over sodium sulfate and evaporated. Concentrated HCl (5 ml) in ethanol (300 ml) was added to the residue and solvents were removed under vacuum. Tetrahydrochloride salt was recrystallized in 3% aqueous EtOH to give 2.91 g (68%) of (4) as a white solid: NMR (D$_2$O/TSP) δ 1.15–2.09 (m, 18H), 2.75–3.59 (m, 16H). Anal. calcd. for $C_{18}H_{42}Cl_4N_4$: C-47.37, H-9.28, N-12.28. Found: C-47.25, H-9.35, N-12.17.

Example 4

Figure 6:
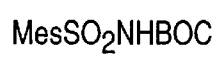
Figure 6:
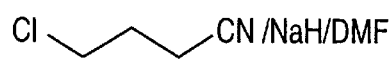
Figure 6:
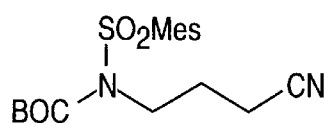
Figure 6:
Figure 6:
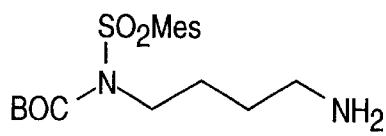
Figure 6:
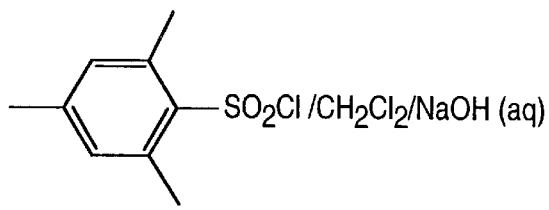
Figure 6:
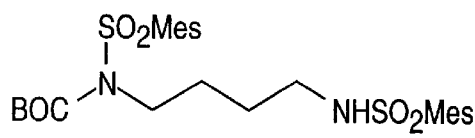

Synthesis of Unsymmetrical Polyamine Analogues [FIGS. 6–8]

As shown in FIG. 6, N-(tert-Butoxycarbonyl)-N-mesitylenesulfonylamide (BOCNHSO$_2$Mes) (1), a di-protected ammonia, was alkylated with 4-chlorobutyronitrile (NaH/DMF) to give (2). The cyano group of (2) was hydrogenated with Raney nickel in methanolic ammonia, resulting in primary amine (3). Both the tert-butoxycarbonyl and mesitylenesulfonyl amine protecting groups were stable to these reduction conditions. Attachment of a second mesitylenesulfonyl functionality to amine (3) under bi-phasic conditions generated the reagent, N-(tert-butoxycarbonyl)-N,N'-bis(mesitylenesulfonyl) putrescine (4). It is noteworthy that this route is flexible, as well, in that an ∞-chloroalkanenitrile of any length can be employed in the alkylation of BOCNHSO$_2$Mes (1).

Another preparation of an unsymmetrical polyamine analogue is shown in FIG. 7. Reagent (1) was deprotonated and alkylated with N-(ethylamino)tetramethylene unit (2), providing (3). After removal of the tert-butoxycarbonyl group under mild acidic conditions (TFA, CH$_2$Cl$_2$) to produce (4), the other nitrogen of the putrescine reagent was elaborated with N-(ethylamino)trimethylene segment (5). Unmasking of the amino groups of (6) generated tetraamine (7), in which the outer chains are unequal.

A further preparation is shown in FIG. 8. N-Ethyl trisulfonamide (3) was alkylated with N-(4-bromobutyl)-N-(tert-butyl)mesitylenesulfonamide (2) to afford masked polyamine (4). Treatment of (4) with HBr/HOAc/PhOH cleanly removed the tert-butyl group, as well as the sulfonamides, giving N$^1$-ethylhomospermine (5), a polyamine analogue metabolite. Only the sulfonamides were cleaved using sodium and liquid ammonia to provide the unsymmetrically dialkylated homospermine derivative (6).

Example 5

NMDA Receptor Modulation by Linear Polyamine Analogues

Membrane Preparation

The procedure for measuring specific binding of [$^3$H]MK-801 to the N-methyl-D-aspartate receptor complex was a modification of the method of Ransom and Stec [J. Neurochem., Vol. 51, pp. 830–836 (1988)]. Cerebral cortices from young male Sprague-Dawley rats (200–300 g) were homogenized with 10 volumes of ice-cold 0.32M sucrose using a motor-driven glass/Teflon homogenizer. The homogenate was centrifuged at 1,000 g for 10 minutes. The 1,000 g pellet was re-suspended in buffer A (5 mM Tris-HCl, pH 7.7 at 4° C.) and centrifuged at 8,000 g for 20 minutes. The supernatant and upper buffy coat of the pellet were combined and centrifuged at 50,000 g for 20 minutes. The pellet was then re-suspended in 10 volumes of buffer A and homogenized using high-intensity ultrasound and centrifuged at 50,000 g, discarding the supernatant. The pellet was washed in this manner an additional three times and stored as a frozen suspension at 80° C. for at least 18 hours, but no longer than two weeks, before use.

Binding Assay

For binding experiments, frozen membranes were thawed, pelleted at 50,000 g for 20 minutes and washed as described above, except that 20 volumes of buffer A were used for re-suspension, for a total of five times. The final pellet was re-suspended in buffer B (5 mM Tris-HCl, pH 7.5 at 23° C.). The binding assay mixture was 1.00 ml of buffer B containing 200–300 μg of membrane protein (Lowry method), 100 μM L-glutamate (L-Glu), 100 μM glycine (Gly), 2 nM [$^3$H]MK-801 and tetraamine at the following concentrations: 0 ("100%+L-Glu+Gly Control") and 0.05, 0.1, 0.5, 1, 5, 10, 50, 100, 500 and 1,000 μM. Non-specific binding was determined using 100 μM MK-801.

Binding assays were performed in triplicate at 23° C. for 1 hour and were terminated by filtration through Whatman GF/B glass fiber filters followed by three 5.0 ml rinses of ice-cold buffer B using a Brandel M-48 cell harvester. Each tetraamine was tested on at least three different preparations of rat cortical membranes, always with comparable results.

The spermine (SPM) curve is a biphasic "bell shape" with increased binding of [$^3$H]MK-801 relative to the "100% Control" observed at spermine concentrations between 1 and 100 $\mu$M (see FIG. 2). At 500 and 1,000 $\mu$M, SPM exhibits moderate antagonism of [$^3$H]MK-801 binding relative to the "100% Control": 500 $\mu$M SPM (82.0±8.1) and 1,000 $\mu$M SPM (78.9±8.3). At 1 $\mu$M, all of the polyamines except DBHSPM and BAHSPM displayed clear agonist activity: SPM (123.2±5.0), DMNSPM (120.6±3.1), DMHSPM (117.8±8.1), DENSPM (113.7±5.9), DEHSPM (114.3±4.5), DBHSPM (106.5±8.0) and BAHSPM (101.9±4.0). At 10 $\mu$M, all the analogues displayed significant (p<0.01) antagonist activity relative to the "100% Control": DMNSPM (87.9±6.0), DMHSPM (76.3±7.0), DENSPM (63.7±5.9), DEHSPM (53.9±6.0), DBHSPM (33.0±4.0) and BAHSPM (15.0±4.0). Thus, the potency as an antagonist correlates to the size of the terminal alkyl groups, i.e., adamantyl>tert-butyl>ethyl>methyl.

Example 6

NMDA Receptor Modulation by Piperidine Polyamine Analogues

Using the method described in Example 1, binding assays were conducted with piperidine polyamine analogues. Each binding assay mixture was 1.00 ml of buffer B containing 200–300 $\mu$g of membrane protein (Lowry method), 100 $\mu$M L-glutamate (L-Glu), 100 $\mu$M glycine (Gly), 2 nM [$^3$H]MK-801 and piperidine polyamine at the following concentrations: 0 ("100%+L-Glu+Gly Control") and 0.05, 0.1, 0.5, 1, 5, 10, 50, 100, 500 and 1,000 $\mu$M. At 0–12 $\mu$M, all of the piperidine polyamines except PIP[5,4,5] displayed clear agonist activity: PIP[4,4,4] is antagonistic above 12 $\mu$m, PIP[3,4,3] is agonistic even at 100 $\mu$m, and PIP[3,3,3] is still agonistic at 100 $\mu$m. PIP[5,4,5] is antagonistic above 13 $\mu$m.

Example 7

Protocol for Determination of Improvement of Cognitive Function in Humans

General Procedures

Five otherwise healthy volunteers with evidence of early stage Alzheimer's Disease as determined by the NINCDS-ADRDA criteria [McKhann et al., Neurology, Vol. 34, pp. 939–944 (1984)] and five healthy volunteers with no NINCDS-ADRDA evidence of AD (control group) of both sexes aged 60–75 years are admitted to a single blind study. Patients undergo the following procedures in a randomized fashion:

1. Baseline: registration of EEG (electroencephalogram), psychometric testing (Short-Term Memory Test and Mini Mental State Examination), assessment of P-300 potential by audiometric testing.
2. The same evaluations after receiving daily intravenous (i.v.) placebo (vehicle) for two weeks.
3. The same evaluations after receiving daily i.v. active ingredient in vehicle.

Each of phases 1 to 3 is followed by a period of at least two weeks before starting the next one. Every patient undergoes all 3 phases. Active ingredient is diethylhomospermine (DEHSPM) at a dosage level of 1.5 mg/kg in physiological saline made with water for injection. Results from each phase of the investigation are compared against the other two phases for each patient. Conventional statistical methods, including determination of a "p" value, are used to evaluate the data for the control group vs. the patients with diagnosed AD to determine the efficacy of the active ingredient.

Psychometric Evaluation: Short-term Memory Test

The memory test consists in the memorization of a list of neutral words. The investigator reads the words; then a dispersion phase ensues, consisting in the performance of some arithmetical tasks. The subject is then asked to repeat as many words from the list as he or she could remember. The words used in each case are different, in order to avoid learning.

Psychometric Evaluation: Short-term Memory Test

The Mini Mental State Examination (MMSE) of Folstein et al. [J. Psychiatr. Res., Vol. 12, pp. 189–198 (1975)] is a series of short tests that determine orientation, registration, attention, calculation ability, recall, language and praxis. The examination is widely used for dementia screening, since it is simple and can be rapidly administered to document cognitive dysfunction. An MMSE score of 23 or lower is used as an indication of sufficient cognitive decline for the diagnosis of dementia.

Assessment of P-300 Potential by Audiometric Testing

The aim of this test is to study the evoked potential P-300, known to be related with the attention span required to follow up and memorize a phenomenon. After an auditive stimulus, the mechanisms involved in the process of the hearing produce bioelectric activity directly related to the stimulus itself. The perception process is more complex that the mere "hearing" and even after the stimulus has been removed, the bioelectric activity related to it can be observed, as a form of "echoes." These "echoes" are the evoked potentials. P-300 is a positive wave that can be observed 300 milliseconds after the first peak due to stimulus and is known to be related with the conscious processing of it, namely with the attention devoted to it. The subject hears some beeps of either 1,000 or 2,000 hertz, given in a random way. He or she is then asked to say how many high beeps (2,000 hertz) were sent.

EEG Monitoring

After a baseline is established, EEG monitoring starts one week after administration of the test article. Each session lasts about one hour. EEG mapping is performed with a PATHFINDER device. A first screening of the maps for each frequency band (alpha, beta 1, beta 2, delta and theta) is performed, as well as for P-300. Changes are defined as any variation in amplitude (potential) or in topographical distribution of the bands and are studied subject by subject, comparing the pattern obtained after injection of the test article versus baseline recording and versus placebo.

Unless defined otherwise, all technical and scientific terms used herein have the same meaning as commonly understood by one of ordinary skill in the art to which this invention belongs.

It is understood that the examples and embodiments described herein are for illustrative purposes only and that various modifications or changes in light thereof will be suggested to persons skilled in the art and are to be included within the scope of the application and the appended claims.

We claim:

1. A method for modulating neurological function in a compromised mammalian host, said method comprising:

administering a therapeutically effective amount of a polyamine having the formula:

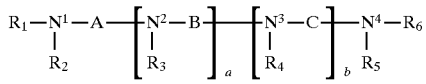

or a pharmaceutically acceptable acid-addition salt thereof, wherein:

each of $R_1$, $R_2$, $R_3$, $R_4$, $R_5$ and $R_6$ may be the same or different and each is hydrogen, alkyl, hydrocarbyl aryl, hydrocarbyl aryl alkyl, cycloalkyl, or any of the foregoing wherein the alkyl chain is interrupted by at least one etheric oxygen atom;

each of $N^1$, $N^2$, $N^3$ and $N^4$ is a nitrogen atom capable of protonation at physiological pH's;

a and b may be the same or different and each is an integer from 1 to 4;

A, B and C may be the same or different and each of A, B and C is alkylene, branched alkylene, cycloalkylene, hydrocarbyl arylalkylene or a heterocyclic bridging group wherein at least one of said $N^1$, $N^2$, $N^3$ or $N^4$ atoms is incorporated in the ring as the hetero atom.

2. A method according to claim 1, wherein said modulating is increasing and said neurological function is cognitive function.

3. A method according to claim 1, wherein:

each of a and b is 1;

each of A and C is —$(CH_2)_n$— and B is —$(CH_2)_m$— wherein n and m may be the same or different and each is an integer from 1 to 6;

each of $R_1$ and $R_6$ is $C_{1-12}$ alkyl or cycloalkyl; and each of $R_2$, $R_3$, $R_4$ and $R_5$ is hydrogen.

4. A method according to claim 3, wherein each of $R_1$ and $R_6$ is methyl.

5. A method according to claim 3, wherein each of $R_1$ and $R_6$ is ethyl.

6. A method according to claim 4 or 5, wherein each of n and m is 3.

7. A method according to claim 4 or 5, wherein each of n and m is 4.

8. A method according to claim 4 or 5, wherein n is 3 and m is 4.

9. A method according to claim 3, wherein each of n and m is 4 and each of $R_1$ and $R_6$ is adamantyl.

10. A method according to claim 3, wherein n is 2 and m is 4.

11. A method according to claim 3, wherein n is 1 and m is 3 or 4.

12. A method according to claim 3, wherein n is 0 and m is 3 or 4.

13. A method for treating Alzheimer's disease, said method comprising:

administering a therapeutically effective amount of a polyamine having the formula:

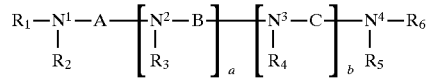

or a pharmaceutically acceptable acid-addition salt thereof, sufficient to increase cognitive function, wherein:

each of $R_1$, $R_2$, $R_3$, $R_4$, $R_5$ and $R_6$ may be the same or different and each is hydrogen, alkyl, hydrocarbyl aryl, hydrocarbyl aryl alkyl, cycloalkyl, or any of the foregoing wherein the alkyl chain is interrupted by at least one etheric oxygen atom;

each of $N^1$, $N^2$, $N^3$ and $N^4$ is a nitrogen atom capable of protonation at physiological pH's;

a and b may be the same or different and each is an integer from 1 to 4;

A, B and C may be the same or different and each of A, B and C is alkylene, branched alkylene, cycloalkylene, hydrocarbyl arylalkylene or a heterocyclic bridging group wherein at least one of said $N^1$, $N^2$, $N^3$ or $N^4$ atoms is incorporated in the ring as the hetero atom.

14. A method according to claim 13, wherein:

each of a and b is 1;

each of A and C is —$(CH_2)_n$— and B is —$(CH_2)_m$— wherein n and m may be the same or different and each is an integer from 1 to 6;

each of $R_1$ and $R_6$ is $C_{1-12}$ alkyl or cycloalkyl; and each of $R_2$, $R_3$, $R_4$ and $R_5$ is hydrogen.

15. A method according to claim 14, wherein each of $R_1$ and $R_6$ is methyl.

16. A method according to claim 14, wherein each of $R_1$ and $R_6$ is ethyl.

17. A method according to claim 15 or 16, wherein each of n and m is 3.

18. A method according to claim 15 or 16, wherein each of n and m is 4.

19. A method according to claim 15 or 16, wherein n and m are 4.

20. A method according to claim 13, wherein n is 2 and m is 4.

21. A method according to claim 13, wherein n is 1 and m is 3 or 4.

22. A method according to claim 13, wherein n is 0 and m is 3 or 4.

23. A pharmaceutical composition for the treatment of neurodegeneration in a mammal afflicted therewith comprising a therapeutically effective amount of a polyamine and a pharmaceutically acceptable carrier therefor, said Polyamine having the formula:

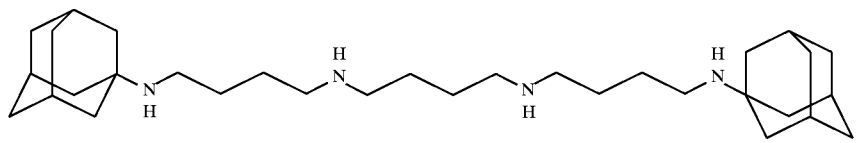

or a pharmaceutically acceptable acid-addition salt thereof.

* * * * *